United States Patent
Tanabe

(10) Patent No.: US 12,292,492 B2
(45) Date of Patent: May 6, 2025

(54) METHOD AND APPARATUS FOR HOMOGENIZING MAGNETOSTATIC FIELD GENERATED FROM SUPERCONDUCTING MAGNET

(71) Applicant: CANON MEDICAL SYSTEMS CORPORATION, Otawara (JP)

(72) Inventor: Hajime Tanabe, Okayama (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 151 days.

(21) Appl. No.: 18/171,796

(22) Filed: Feb. 21, 2023

(65) Prior Publication Data
US 2023/0280426 A1      Sep. 7, 2023

Related U.S. Application Data

(63) Continuation of application No. PCT/JP2020/032031, filed on Aug. 25, 2020.

(51) Int. Cl.
*G01R 33/38* (2006.01)
*G01R 33/3815* (2006.01)
*G01R 33/3873* (2006.01)

(52) U.S. Cl.
CPC ..... *G01R 33/3873* (2013.01); *G01R 33/3815* (2013.01)

(58) Field of Classification Search
CPC .............. G01R 33/3806; G01R 33/421; G01R 33/381; G01R 33/3815; G01R 33/3873; A61B 5/055; H01F 7/0278
See application file for complete search history.

(56) References Cited

U.S. PATENT DOCUMENTS 4,924,185 A * 5/1990 Matsutani ............ G01R 33/421
                                                               324/319
8,604,793 B2 * 12/2013 Shen .................. G01R 33/3873
                                                               324/319
(Continued)

FOREIGN PATENT DOCUMENTS

JP      2016-152898 A      8/2016
JP      2018-196776 A     12/2018
(Continued)

OTHER PUBLICATIONS

International Search Report issued Oct. 13, 2020 in PCT/JP2020/032031 filed Aug. 25, 2020, 2 pages.

*Primary Examiner* — Vinh P Nguyen
(74) *Attorney, Agent, or Firm* — Oblon, McClelland, Maier & Neustadt, L.L.P.

(57) ABSTRACT

A method includes: calculating a first optimum quantity of ferromagnetic arranged at each position so that each error component of a magnetic field distribution in a specific space satisfies a first restriction condition (S33, S34); discretizing, for each position, the first optimum quantity (S35); calculating the error components that are obtained when ferromagnetic having a quantity of the first combination is arranged at each position (S36); when the error component is less than the first lower limit, setting a condition including a lower limit greater than the first lower limit and an upper limit greater than the first upper limit as a second restriction condition, and when the error component is greater than the first upper limit, setting a condition including a lower limit less than the first lower limit and an upper limit less than the first upper limit as a second restriction condition (S38).

4 Claims, 7 Drawing Sheets

(56) References Cited

U.S. PATENT DOCUMENTS

| | | | |
|---|---|---|---|
| 8,781,197 B2* | 7/2014 | Wang | G01R 33/54 |
| | | | 382/131 |
| 9,964,613 B2* | 5/2018 | Abe | G01R 33/3873 |
| 10,514,432 B2* | 12/2019 | Abe | G01R 33/3873 |
| 12,027,309 B2* | 7/2024 | Iwamoto | H01F 6/04 |
| 2016/0146912 A1 | 5/2016 | Abe | |
| 2018/0031650 A1 | 2/2018 | Abe et al. | |
| 2018/0284205 A1 | 10/2018 | Sakakibara et al. | |

FOREIGN PATENT DOCUMENTS

| | | |
|---|---|---|
| WO | WO 2015/005109 A1 | 1/2015 |
| WO | WO 2016/132832 A1 | 8/2016 |

* cited by examiner

METHOD AND APPARATUS FOR HOMOGENIZING MAGNETOSTATIC FIELD GENERATED FROM SUPERCONDUCTING MAGNET

CROSS-REFERENCE TO RELATED APPLICATIONS

This application is based upon and claims the benefit of priority from International Patent Application No. PCT/JP2020/032031, filed on Aug. 25, 2020, the entire contents of which are incorporated herein by reference.

FIELD

Embodiments described herein relate generally to a method and an apparatus for homogenizing a magnetostatic field generated from a superconducting magnet.

BACKGROUND

There have been known methods (shimming) for homogenizing a magnetostatic field generated from a superconducting magnet. Japanese Laid-open Patent Publication No. 2016-152898 (Patent Literature 1), for example, discloses a method for adjusting a magnetic homogeneity by a magnetostatic-field generating apparatus including a shim tray on which magnetic pieces are arranged. This magnetic homogeneity adjusting method can efficiently adjust the magnetic homogeneity to a high level even when there is an upper limit in quantity about magnetic pieces possible to arrange on the shim tray.

The magnetic homogeneity adjusting method disclosed in Patent Literature 1 includes changing a target magnetic field for the magnetostatic-field generating apparatus within a predetermined range to select such a target magnetic field that has a minimum magnetic homogeneity of the magnetostatic field. As a result, it is taken into consideration an error (discretization error) between the quantity of magnetic pieces calculated in shimming for the homogenization of magnetostatic field and the actual discrete quantity of magnetic pieces. However, any discretization error is still present in the target magnetic field that has been selected finally. Accordingly, there is room for improvement in the homogenization of magnetostatic field by the magnetic homogeneity adjusting method.

DETAILED DESCRIPTION

Figure 1:
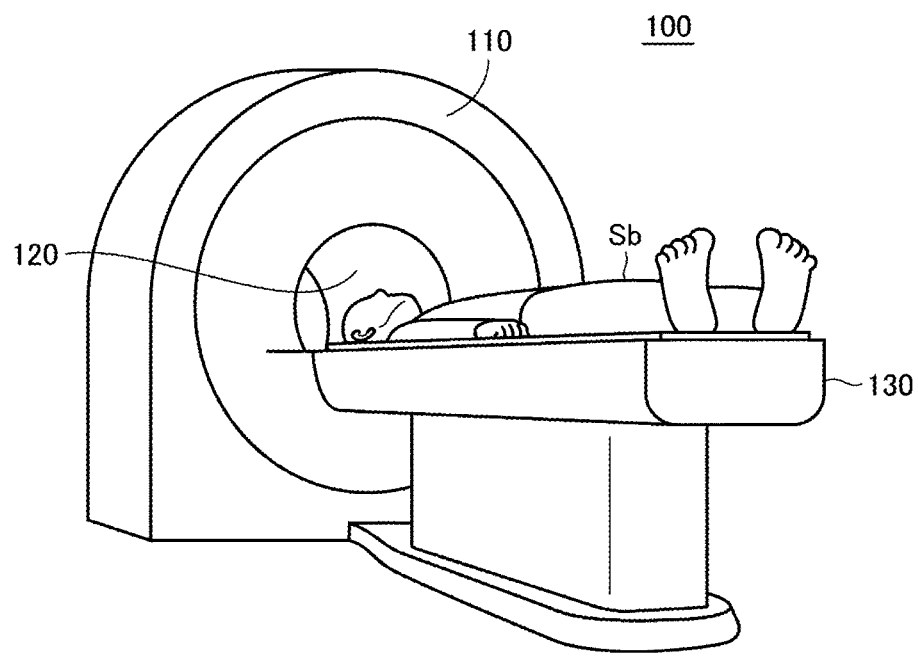
FIG. 1 is a perspective view illustrating an exterior appearance of a magnetic resonance imaging (MRI) apparatus according to a first embodiment.

An embodiment of the present invention provides a method of homogenizing, in a specific space, a magnetostatic field generated from a superconducting magnet by arranging a plurality of ferromagnetic bodies in the specific space, the specific space being subjected to the magnetostatic field, wherein a plurality of positions in the specific space at which the plurality of ferromagnetic bodies are arranged are predetermined, and each of the plurality of ferromagnetic bodies is selected from a plurality of specific ferromagnetic bodies each having a predetermined quantity. The method includes: setting a first restriction condition including a first lower limit and a first upper limit for each of a plurality of error components of a magnetic field distribution in the specific space, and calculating a first optimum quantity of ferromagnetic arranged at each of the plurality of positions so that the error component satisfies the first restriction condition corresponding to the error component; calculating, for each of the plurality of positions, a first combination of at least one ferromagnetic body selected from the plurality of specific ferromagnetic bodies, the first combination having a minimum error from the first optimum quantity corresponding to the position; calculating the plurality of error components that are obtained when ferromagnetic having the quantity of the first combination is arranged at each of the plurality of positions; when, for each of the plurality of error components, the error component is less than the first lower limit corresponding to the error component, setting a condition including a lower limit that is greater than the first lower limit and an upper limit that is greater than the first upper limit as a second restriction condition, and when the error component is greater than the first upper limit corresponding to the error component, setting a condition including a lower limit that is less than the first lower limit and an upper limit that is less than the first upper limit as a second restriction condition, and calculating a second optimum quantity of ferromagnetic arranged at each of the plurality of positions so that the error component satisfies the second restriction condition corresponding to the error component; and calculating, for each of the plurality of positions, a second combination of at least one ferromagnetic body selected from the plurality of specific ferromagnetic bodies, the second combination having a minimum error from the second optimum quantity corresponding to the position.

An object of the embodiments is to improve homogeneity of a magnetostatic field generated by a superconducting magnet. A magnetic homogeneity adjusting method according to a present embodiment includes, for each of a plurality of error components, when the error component is less than a first lower limit corresponding to that error component, setting a condition including a lower limit greater than the first lower limit and an upper limit greater than a first upper limit as a second restriction condition; and when the error component is greater than the first upper limit corresponding to that error component, setting a condition including a lower limit less than the first lower limit and an upper limit less than the first upper limit as the second restriction condition. This enables improvement in the homogenization of the magnetostatic field generated by the superconducting magnet.

Embodiments of the present disclosure will be explained in detail below with reference to the accompanying drawings. Note that the same or correspondent components are denoted with the same reference numerals or signs in the drawings, and their explanations are not repeated in principle.

First Embodiment

FIG. 1 is a perspective view illustrating an exterior appearance of a magnetic resonance imaging (MRI) apparatus 100 according to a first embodiment. As illustrated in FIG. 1, the MRI apparatus 100 includes a magnetostatic field generator 110 and a table 130 on which a subject Sb lies. The magnetostatic field generator 110 includes a cylindrical superconducting magnet. The superconducting magnet generates a magnetostatic field inside a bore 120 that is shaped as a tunnel with a hollow center. Note that the MRI apparatus 100 according to the first embodiment is not limited to a cylindrical type, and it may be an opened type. In an opened-type MRI apparatus, groups of superconducting magnets face each other with a fixed gap therebetween in either up-and-down directions or left-and-right directions, and the subject is placed in the gap.

Figure 2:
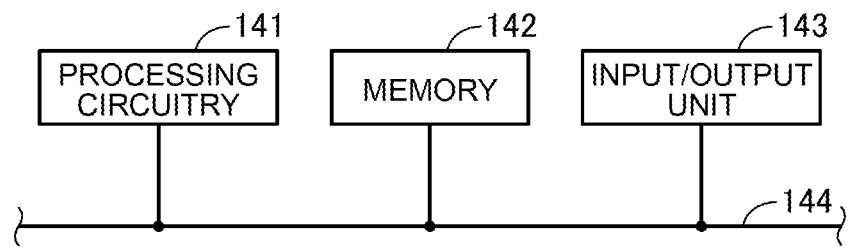
FIG. 2 is a function block diagram illustrating structure of an information processing apparatus for magnetic-field adjustment calculation for the MRI apparatus illustrated in FIG. 1.

FIG. 2 is a function block diagram illustrating structure of an information processing apparatus 140 for magnetic-field adjustment calculation for the MRI apparatus 100 illustrated in FIG. 1. As illustrated in FIG. 2, the information processing apparatus 140 includes processing circuitry 141, a memory 142, and an input/output unit 143. The processing circuitry 141, the memory 142, and the input/output unit 143 are coupled to each other via a bus 144. The information processing apparatus 140 is a separate apparatus from the MRI apparatus 100, and the information processing apparatus 140 includes a personal computer or a workstation, for example.

The processing circuitry 141 may be dedicated hardware or a central processing unit (CPU) that runs a program stored in the memory 142. When the processing circuitry 141 is dedicated hardware, the processing circuitry 141 corresponds to, for example, single circuitry, composite circuitry, a programmed processor, a parallel-programmed processor, an application specific integrated circuit (ASIC), or a field programmable gate array (FPGA), or any combination thereof. When the processing circuitry 141 is a CPU, functions of the information processing apparatus 140 are implemented by software, firmware, or a combination of software and firmware. The software or firmware is described as a program and stored in the memory 142. The processing circuitry 141 reads the program stored in the memory 142 and executes the program. The memory 142 stores therein a magnet-field adjusting program (specific program), for example. Note that the CPU may also be referred to as a central processor, a processing apparatus, an arithmetic apparatus, a microprocessor, a microcomputer, a processor, or a digital signal processor (DSP). The memory 142 includes nonvolatile or volatile semiconductor memories (for example, random access memory (RAM), read only memory (ROM), flash memory, erasable programmable read only memory (EPROM), or electrically erasable programmable read only memory (EEPROM)), magnetic disk, flexible disk, optical disc, compact disc, minidisc, or digital versatile disc (DVD).

Figure 3:
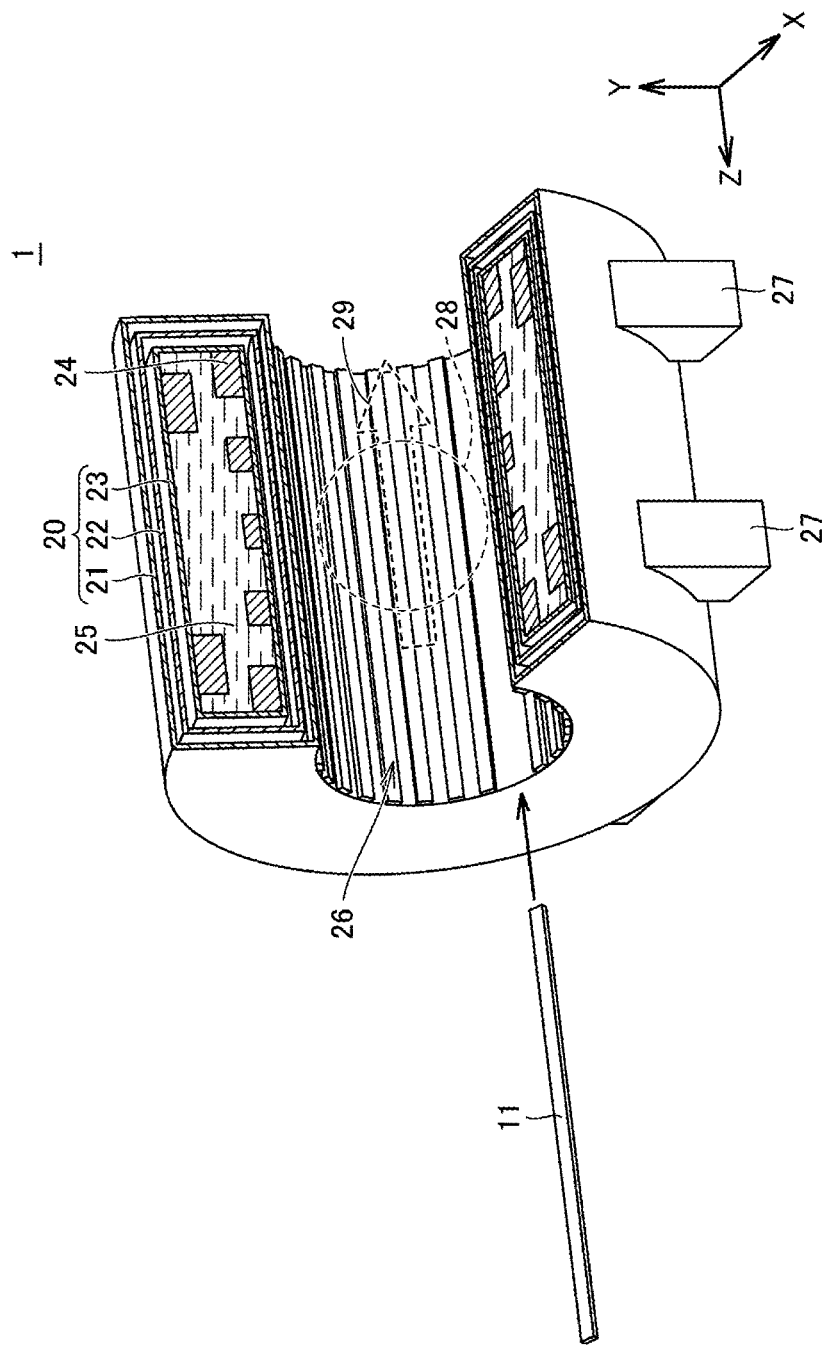
FIG. 3 is a cross-sectional view illustrating structure of a superconducting magnet included in a magnetostatic field generator as illustrated in FIG. 1.

The input/output unit 143 receives an operation from a user and outputs a processing result of the processing circuitry 141 to the user. The input/output unit 143 includes a mouse, a keyboard, a touch panel, a display, and a speaker, for example, FIG. 3 is a cross-sectional view illustrating structure of a superconducting magnet 1 included in the magnetostatic field generator 110 as illustrated in FIG. 1. X, Y, and Z axes in FIG. 3 are orthogonal to each other. As illustrated in FIG. 3, the superconducting magnet 1 is a cylindrical type. The superconducting magnet 1 includes a cryostat 20 operating as a heat-insulated container and a plurality of shim trays 11. The cryostat 20 includes a vacuum vessel 21, a heat shield 22, and a helium vessel 23. Note that the plurality of shim trays 11 may be attached to the superconducting magnet 1 via a structural object (not illustrated) separate from the superconducting magnet 1.

The hollow cylindrical vacuum vessel 21 is disposed on the outermost of the cryostat 20. A space at the cylinder center portion of the vacuum vessel 21 is a bore portion 26 (specific space) that corresponds to the bore 120. The inside of the vacuum vessel 21 is depressurized to be vacuum by a not-illustrated decompression apparatus. The vacuum vessel 21 is supported by leg portions 27 disposed at the bottom so that the center axis of the bore portion 26 is parallel to the Z axis.

The heat shield 22 is disposed inside the vacuum vessel 21, the heat shield 22 having a hollow cylindrical shape that is substantially similar to the vacuum vessel 21. The helium vessel 23 is disposed inside the heat shield 22, the helium vessel 23 having a hollow cylindrical shape that is substantially similar to the heat shield 22. The heat shield 22 has a function to insulate heat between the helium vessel 23 and the vacuum vessel 21.

There is a superconducting coil 24 disposed on an inner periphery of the helium vessel 23. The inside of the helium vessel 23 is filled with a liquid helium 25. The superconducting coil 24 is soaked and cooled in the liquid helium 25.

When the superconducting magnet 1 operates, a magnetostatic field 29 extending in the Z axis direction is generated in a magnetic field space 28 (imaging space) of the bore portion 26. For clear imaging in the magnetic field space 28, it is needed to make the inside of the magnetic field space 28 homogeneous as high as the order of parts per million (ppm). For this purpose, the superconducting magnet 1 is optimized in the designing phase to realize the high magnetic homogeneity.

However, due to a manufacturing error, etc., the superconducting magnet 1 usually has a magnetic homogeneity as low as about hundreds to thousands ppm at the time of completion of the real machine. Therefore, adjustment of magnet homogeneity (shimming) is usually performed after the superconducting magnet 1 has been manufactured. Types of shim that is a structural component (for example, a coil or an iron piece) used to carry out shimming include: superconducting shim, normal-conducting shim, and iron shim, for example.

In a shimming that uses superconducting shims, there are arranged a plurality of superconducting coils independently and separated from the superconducting coil that generates a main magnetostatic field for MRI imaging. This shimming includes flowing a current to each of the plurality of superconducting coils, the current being optimized in accordance with the superconducting coil, and adjusting the magnetic homogeneity by a magnetic field generated from the superconducting coil. In a shimming that uses normal-conducting shims, normal-conducting coils are used instead of the super-conducting coils.

In a shimming that uses iron shims, there are a plurality of iron pieces (iron shims) of ferromagnetic bodies, each being arranged at an optimum position in the bore portion 26. The iron shims are magnetized by the magnetostatic field 29 generated by the superconducting magnet 1, and the shimming is performed using magnetic fields generated by the iron shims. Note that silicon steel sheets are usually used as the iron shims because of the saturated flux density, the variability in quality, etc. Permanent magnets may be used as the iron shims.

The shimming that uses superconducting shims and the shimming that uses normal-conducting shims are advantageous in that the shimming can be carried out accurately by fine-tuning of current, the operation is easy, etc. The superconducting shims especially have great shimming ability because the superconducting shims can make a current flowing therethrough greater. However, for the superconducting shims and the normal-conducting shims, it is necessary to take into consideration magnetic coupling of the superconducting coil that generates the main magnetostatic field 29 over the normal-conducting coils. Moreover, because the superconducting shims and the normal-conducting shims cannot generate a complex asymmetric-magnetic-field, their shimming has a low degree of freedom. In addition, the shimming that uses superconducting shims and the shimming that uses normal-conducting shims are likely to cost high, relatively. In the shimming that uses superconducting shims and the shimming that uses normal-conducting shims, when the current in the shims is attenuated or changed due to any failure, the magnetic homogeneity in the magnetic field space 28 may become worse.

Advantages and disadvantages of the shimming that uses iron shims are substantively opposite to the advantages and disadvantages of the shimming that uses superconducting shims and the shimming that uses normal-conducting shims. The shimming that uses iron shims, however, has a fine-tuning ability necessary and sufficient to achieve accurate shimming. Moreover, the iron shims has the shimming ability with a necessary-and-sufficient level.

The superconducting magnet 1 performs shimming using iron shims. The iron shims are accommodated in the shim trays 11 as illustrated in FIG. 3. To enhance the degree of freedom in shimming, the plurality of shim trays 11 are arranged on the inner periphery of the bore portion 26 at a predetermined pitch (for example, a pitch of 15° viewed in the Z axis direction). Note that the plurality of shim trays 11 may be arranged on the bore portion 26 via a separate apparatus from the superconducting magnet 1. In an opened-type MRI apparatus, the iron shims are arranged between the groups of superconducting magnets that face each other.

Figure 4:
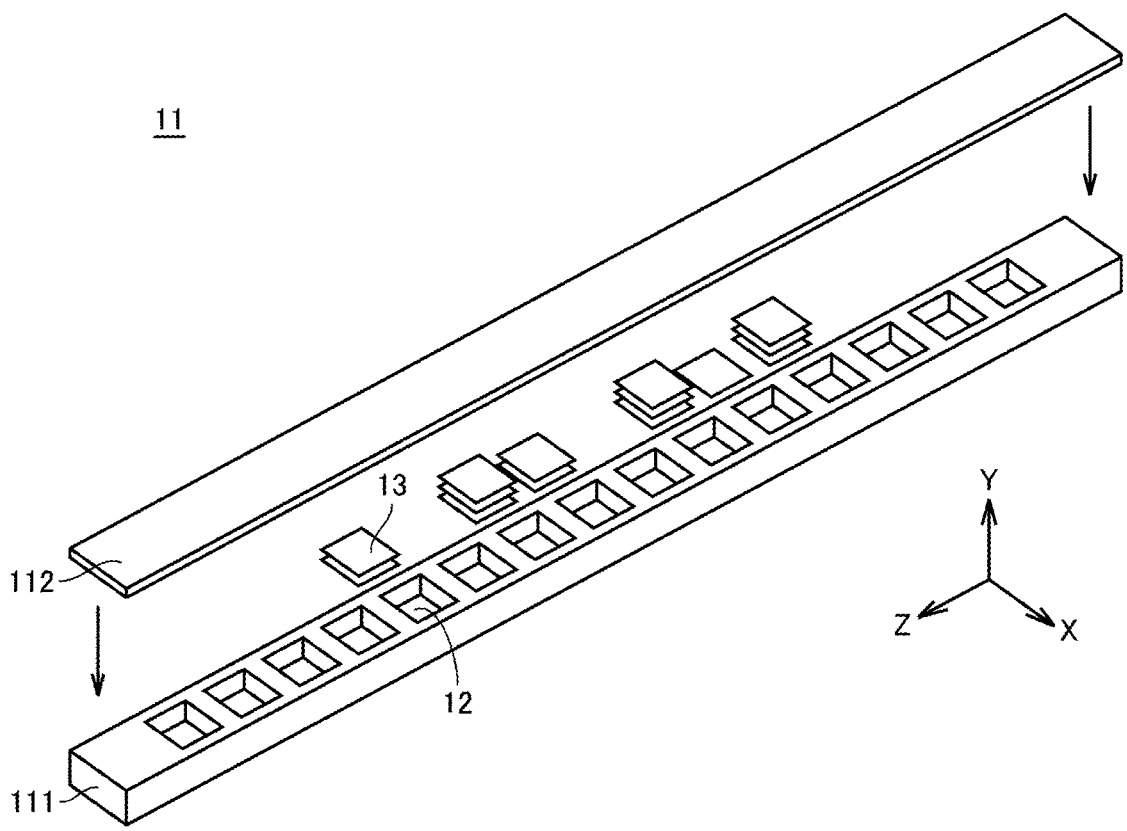
FIG. 4 is an exploded perspective view of a shim tray as illustrated in FIG. 1.

FIG. 4 is an exploded perspective view of the shim tray as illustrated in FIG. 3. As illustrated in FIG. 4, the shim tray 11 includes a body 111 and a cover 112. The body 111 has a bar shape extending in the Z axis direction. A plurality of shim pockets 12 is formed on the body 111, each having a depth in the Y axis direction. A plurality of iron shims 13 is accommodated in the plurality of shim pockets 12. Note that it is not necessary to form the cover 112 in one unit. The cover 112 may include a plurality of covers, each corresponding to one of the plurality of shim pockets 12.

Note that all of the plurality of shim pockets 12 do not need to have the same dimensions; however, they usually have the same dimensions for the sake of efficiency in operations and costs. Therefore, in general, the long-sided length (the Z axis direction in FIG. 4) of each of the plurality of iron shims 13 is equal to each other, and the short-sided length (the X axis direction in FIG. 4) of each of the plurality of iron shims 13 is equal to each other.

The structure to which the iron shims 13 are attached is not necessarily formed as a pocket shape. That structure may be, for example, a structure in which an iron shim with a hole formed thereon is attached to a screw rod provided on the shim tray. Moreover, any structure may be used to attach an iron shim to the superconducting magnet 1. For example, such a structure is allowable that an iron shim is directly attached to a screw rod without any shim tray, the screw rod being directly provided on the bore portion 26 of the superconducting magnet 1.

Figure 5:
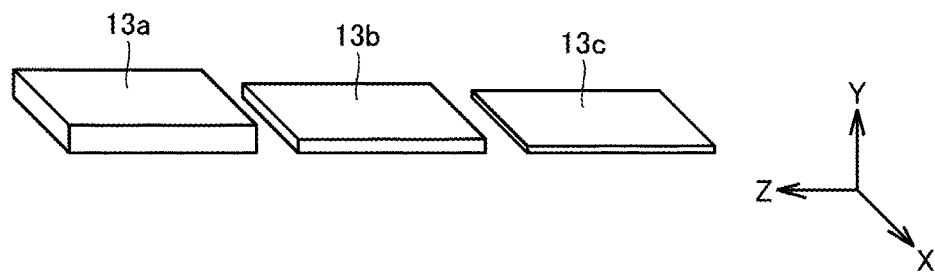
FIG. 5 is a diagram illustrating types of iron shims as illustrated in FIG. 4.

FIG. 5 is a diagram illustrating types of the iron shims 13 as illustrated in FIG. 4. As illustrated in FIG. 5, each of the plurality of iron shims 13 is selected from iron shims 13a, 13b, and 13c (specific ferromagnetic bodies) having predetermined thicknesses (lengths in the Y axis direction). Each of the iron shims 13a to 13c is made of the same iron material and has a normal line extending in the Y axis direction. The length of each of the iron shims 13a to 13c in the Z axis direction is equal to each other. A thickness of the iron shim 13a is thicker than a thickness of the iron shim 13b. The thickness of the iron shim 13b is thicker than a thickness of the iron shim 13c. In other words, a weight of the iron shim 13a is heavier than a weight of the iron shim 13b. The weight of the iron shim 13b is heavier than a weight of the iron shim 13c. For example, the thicknesses of the iron shims 13a, 13b, and 13c are 0.35 mm, 0.10 mm, and 0.05 mm, respectively.

The magnetic homogeneity in the magnetic field space 28 can be improved by adjusting, for each of the plurality of shim trays 11, how many iron shims 13 are accommodated in each of the plurality of shim pockets 12. In the shimming, a magnetic field distribution in the magnetic field space 28 is resolved into two or more error components, and then two or more iron-shim arrangements are optimized such that each of the two or more error components is optimized.

A magnetic field distribution (magnetic field intensity) $B_z$ in the magnetic field space 28 is represented by Expression (1) as follow using Legendre functional expansion:

$$B_z(r, \theta, \phi) = \sum_{\Sigma=n=0}^{\infty} \sum_{\Sigma=m=0}^{n} r^n P_{n,m}(\cos\theta)[A_{n,m}\cos(m\phi) + B_{n,m}\sin(m\phi)] \quad (1)$$

Figure 6:
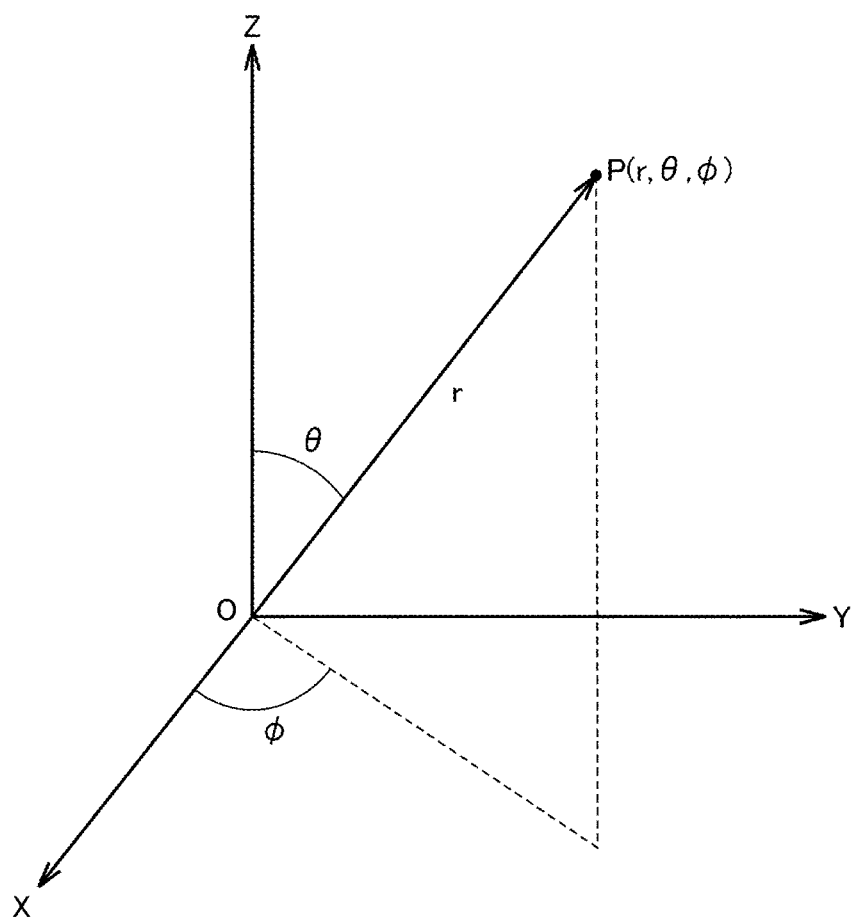
FIG. 6 is a diagram illustrating a polar coordinate system.

The magnetic field distribution $B_z$ as represented by Expression (1) is a magnetic field intensity at a point P (r, θ, φ) in a polar coordinate system as illustrated in FIG. 6. In Expression (1), a distance r is a distance between the origin O and the point P. An angle θ is an angle made between a vector OP and the Z axis. An angle φ is an angle made between a vector obtained by projecting the vector OP on the XY plane and the X axis. In Expression (1), an integer n (≥0) represents the degree, and an integer m (≥0) represents the order. $P_{n,m}$ is a Legendre associated function. $A_{n,m}$ and $B_{n,m}$ are error components, each. In the following explanation, $A_{n,m}$ and $B_{n,m}$ are expressed as A(n, m) and B(n, m), respectively. A(0, 0) and B(0, 0) are not treated as error components. Note that, in the orthogonal coordinate system defined by the X, Y, and Z axes, A(n, m) and B(n, m) may be represented as presented in Expression (2) as follow.

$$A(1, 0) = Z1 \quad (2)$$
$$A(2, 0) = Z2$$

-continued $$A(3, 0) = Z3$$

$$A(4, 0) = Z4$$

$$\vdots$$

$$A(1, 1) = X$$

$$B(1, 1) = Y$$

$$A(2, 1) = ZX$$

$$B(2, 1) = ZY$$

$$A(2, 2) = X^2 - Y^2$$

$$B(2, 2) = XY$$

$$\vdots$$

In the shimming, an optimum quantity of iron shim is arranged in each of the plurality of shim pockets 12 as illustrated in FIG. 4 to make the magnetic field in the magnetic field space 28 homogenous. The optimum quantity of iron shim arranged in each of the plurality of shim pockets 12 is a quantity optimized by the magnetic-field adjusting program to achieve a desired homogeneity of the magnetic field in the magnetic field space 28. In the optimization, a restriction condition is set on each of the plurality of error components obtained by Expression (1), the restriction condition including a lower limit and an upper limit as presented in Expression (3) as follow.

$$-0.3 \le A(1, 0) \le +0.3 \quad (3)$$

$$-0.2 \le A(2, 0) \le +0.2$$

$$-0.2 \le A(3, 0) \le +0.2$$

$$-0.2 \le A(4, 0) \le +0.2$$

$$\vdots$$

$$-0.3 \le A(1, 1) \le +0.3$$

$$-0.3 \le B(1, 1) \le +0.3$$

$$-0.2 \le A(2, 1) \le +0.2$$

$$-0.2 \le B(2, 1) \le +0.2$$

$$-0.2 \le A(2, 2) \le +0.2$$

$$-0.2 \le B(2, 2) \le +0.2$$

$$\vdots$$

The unit of the lower limit and the upper limit of each error component in Expression (3) is ppm. Although Expression (1) indicates that the error components have an infinite number of terms, a finite number of error components is necessary and sufficient to achieve a desired level of the magnetic homogeneity in the magnetic field space 28. The finite number of error components is usually about one hundred to some hundreds. Moreover, depending on an error component, a restriction condition may become relatively large having absolute values as presented in Expression (3) of, for example, 10 ppm or more for the error component, rather than relatively small having absolute values of, for example, 0.2 ppm or 0.3 ppm or less. This is because there is a limitation on a total quantity of iron shim possible to arrange. It is established theoretically and empirically how much restriction condition is imposed on which error component.

The magnetic-field-adjusting-program optimized quantities of iron shim attached to the plurality of shim pockets 12 are determined in thickness, and their values are normalized from 0 to 1. No iron shim is arranged in a shim pocket with a quantity of iron shim of zero. An iron shim with the maximum thickness is arranged in a shim pocket with a quantity of iron shim of one. The maximum thickness is limited by the depth of the shim pocket, and it is predetermined. Depending on a result of optimization by the magnetic-field adjusting program, it is not always that the iron shim is arranged in every pocket of the plurality of shim pockets 12, and some of the shim pockets 12 may have no iron shim arranged.

Suppose, for example, the maximum thickness of iron shim arranged in one of the shim pockets 12 is 10 mm. When the optimum quantity is 1.0, then an iron shim with a thickness of 10 mm is arranged in the shim pocket 12. When the optimum quantity is 0.5, then an iron shim with a thickness of 5 mm is arranged in the shim pocket 12. The optimum quantity calculated by the magnetic-field adjusting program may take consecutive decimal values within a range of effective digits. The optimum quantity may be 0.99998 or 0.000012, for example.

As described above, the optimum quantity (thickness) of iron shim arranged in each of the plurality of shim pockets 12 calculated by the optimization is a consecutive value, which is normalized from 0 to 1. The iron shim actually arranged in each of the plurality of shim pockets 12 is a combination of one or more iron shims selected from the irons shims 13a to 13c as illustrated in FIG. 5. The combination may consist of any one of the irons shims 13a to 13c. For each of the plurality of shim pockets 12, a combination is selected from a finite number of types of iron shims such that the combination is closest to the optimum quantity of iron shim corresponding to the shim pocket 12, and the optimum quantity of iron shim arranged in the shim pocket 12 is discretized.

As a result, for each of the plurality of shim pockets 12, an error (discretization error) occurs between the optimum quantity corresponding to the shim pocket 12 calculated by the magnetic-field adjusting program and the actual quantity of iron shim arranged in the shim pocket 12. The greater the discretization error is, the more each of the plurality of error components in the magnetic field distribution $B_z$ may deviate from an allowable range corresponding to the error component. This may result in an increase in the number of shimming iterations required to achieve the desired level of the magnetic homogeneity in the magnetic field space 28.

A relatively strong electromagnetic force is exerted to the iron shims, and it is difficult to perform shimming during when a magnetic field is generated. Due to this, each time when the number of shimming iterations increases by one, additional operations are required to decrease the intensity of the magnetic field, then rearrange the iron shims, and then increase the intensity of the magnetic field again, etc. Moreover, due to an increase and decrease in the intensity of the magnetic field, the liquid helium for cooling the superconducting magnet 1 is consumed a fixed amount. Because the liquid helium costs relatively high, one additional shimming iteration increases the cost of shimming in addition to the increase in time necessary for the shimming operation.

One possible method to decrease the discretization error includes performing fine-tuning using iron shims as thin as possible. However, extremely-thin iron shims with, for example, about 0.05 mm in thickness may generate a bad effect on workability of shimming, because they are difficult or complicated to handle, etc. A miscount is likely to occur with the extremely-thin iron shims. Moreover, the extremely-thin iron shims tend to cost high in manufacture.

To solve the problems, depending on how much each of the plurality of error components deviates from the allowable range corresponding to the error component, the MRI apparatus 100 resets the restriction condition of the error component so as to cancel out the discretization error. The magnetic homogeneity in the magnetic field space 28 can be improved by re-calculating the optimum quantity of the iron shims 13 arranged in each of the plurality of shim pockets 12 under the reset restriction condition.

Figure 7:
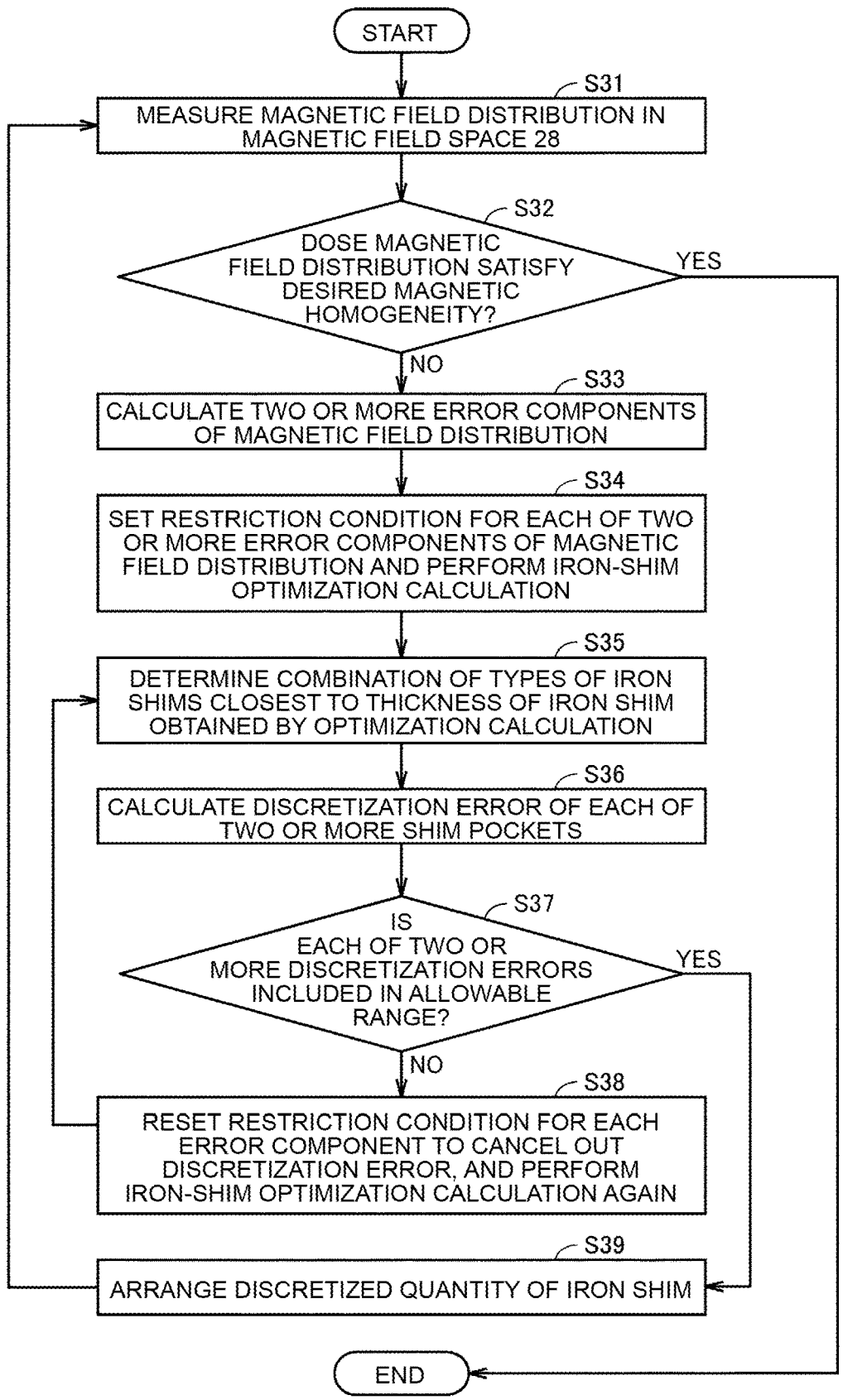
FIG. 7 is a flowchart illustrating a sequence of shimming that is performed on the MRI apparatus as illustrated in FIG. 1.

FIG. 7 is a flowchart illustrating a sequence of shimming that is performed on the MRI apparatus 100 as illustrated in FIG. 1. The wording "step" is simply abbreviated to "S" in the following. S32 to S38 as illustrated in FIG. 7 are implemented when the information processing apparatus 140 executes the magnetic-field adjusting program.

As illustrated in FIG. 7, the magnetic field distribution in the magnetic field space 28 is measured at S31. It is determined at S32 whether the magnetic field distribution measured at S31 satisfies a desired magnetic homogeneity. Whether or not the magnetic field distribution satisfies the desired magnetic homogeneity is determined by, for example, whether or not the magnetic homogeneity is lower than a predetermined threshold.

When the magnetic field distribution measured at S31 satisfies the desired magnetic homogeneity (YES at S32), the shimming is completed. When the magnetic field distribution measured at S31 does not satisfy the desired magnetic homogeneity (NO at S32), two or more error components of the magnetic field distribution $B_z$ are calculated at S33 using Expression (1). At S34, a restriction condition (first restriction condition) is set for each of the two or more error components of the magnetic field distribution, and iron-shim optimization calculation is performed. The optimization calculation optimizes the thickness of iron shim arranged in each of the plurality of shim pockets 12. As a result of the iron-shim optimization calculation at S34, it is calculated, as a calculated ideal value, the thickness corresponding to the quantity (first optimum quantum) of iron shims arranged in each of the plurality of shim pockets 12.

It is calculates at S35 a combination of the iron shims 13*a* to 13*c* for each of the plurality of shim pockets 12 such that the difference in thickness from the calculated ideal value corresponding to the shim pocket 12 becomes minimum. In other words, the quantity (thickness) of iron shim arranged in each of the plurality of shim pockets 12 is discretized at S35. It is calculated at S36 each of the two or more error components of the magnetic field distribution that is obtained when the discretized quantity of iron shim is arranged in each of the plurality of shim pockets 12.

It is determined at S37 whether the discretization error in the quantity of iron shim arranged in each of the plurality of shim pockets 12 is included in a predetermined allowable range. When the discretization error in the quantity of iron shim arranged in each of the plurality of shim pockets 12 is included in the predetermined allowable range (YES at S37), at S39, the quantity of iron shim discretized at S35 is actually arranged in each of the plurality of shim pockets 12, and the process returns to S31.

Suppose, for example, when the restriction condition for the error component $A(1, 0)$ at S34 is $-0.3 \leq A(1, 0) \leq +0.3$, the error component $A(1, 0)$ at S37 is +0.5 ppm. The error component $A(1, 0)$ is beyond the upper limit of the restriction condition. In this example, even when the iron shims are actually arranged in accordance with the quantity of iron shim optimized at S34, it is impossible to obtain the desired magnetic homogeneity because of the discretization error.

To achieve the desired magnetic homogeneity, as the shimming is performed repeatedly so that the magnetic homogeneity is enhanced, the influence of the discretization error is decreased. However, an increase in the number of shimming iterations prolongs the operation time for shimming and, in addition, increases the cost for shimming.

To address this, when the discretization error in the quantity of iron shim arranged in one of the plurality of shim pockets 12 is not included in the allowable range (NO at S37), the restriction condition for each of the plurality of error components in the magnetic field is reset at S38 to cancel out the discretization error. It is calculated at S38 the optimum quantity (second optimum quantity) of iron shim such that the reset restriction condition (second restriction condition) for each error component is satisfied. After the iron-shim optimization calculation is completed at S38, the process returns to S35.

It is performed at S38 when, for each of the plurality of error components in the magnetic field distribution, the error component is less than the lower limit (first lower limit) of the restriction condition set at S34, a condition including a lower limit greater than the lower limit of this restriction condition and an upper limit greater than the upper limit of this restriction condition is set as a new restriction condition. When the error component is greater than the upper limit (first upper limit) of the restriction condition set at S34, a condition including a lower limit less than the lower limit of this restriction condition and an upper limit less than the upper limit of this restriction condition is set as a new restriction condition.

When, for example, the error component $A(1, 0)$ is +0.5 ppm at S37, for example, $-0.6$ ppm $\leq A(1, 0) - 0.4$ ppm is set at S38 as a new restriction condition corresponding to the error component $A(1, 0)$. When the error component $A(1, 0)$ is $-0.5$ ppm at S37, for example, $+0.4$ ppm $\leq A(1, 0) + 0.6$ ppm is set at S38 as a new restriction condition corresponding to the error component $A(1, 0)$. Note that the resetting of the restriction condition is performed individually for each of the plurality of error components. Some error components may have a value within the original restriction condition even when including the discretization error, and the resetting of the restriction condition is not needed for such error components.

When the iron-shim optimization calculation is performed again, an optimum quantity that may be different from the previously calculated one is calculated at S38. The corresponding discretization error may be slightly different from the previous one, but the discretization error is relatively less than the correction amount for each of the plurality of error components. Accordingly, a change in the restriction condition for the error component is relatively less, and the optimization does not provide a new optimum quantity that is remarkably changed from the previous optimum quantity. In other words, as a result of the resetting of the restriction condition to cancel out the discretization errors as appropriate, in most cases, the respective error components at the recalculation results may satisfy their restriction conditions. If, hypothetically, the respective error components at the recalculation results do not satisfy their restriction conditions, when the restriction conditions for the respective error components are reset and recalculated with the same steps, the discretization error decreases one more step. Therefore, the respective error components will satisfy the restriction conditions.

Figure 8:
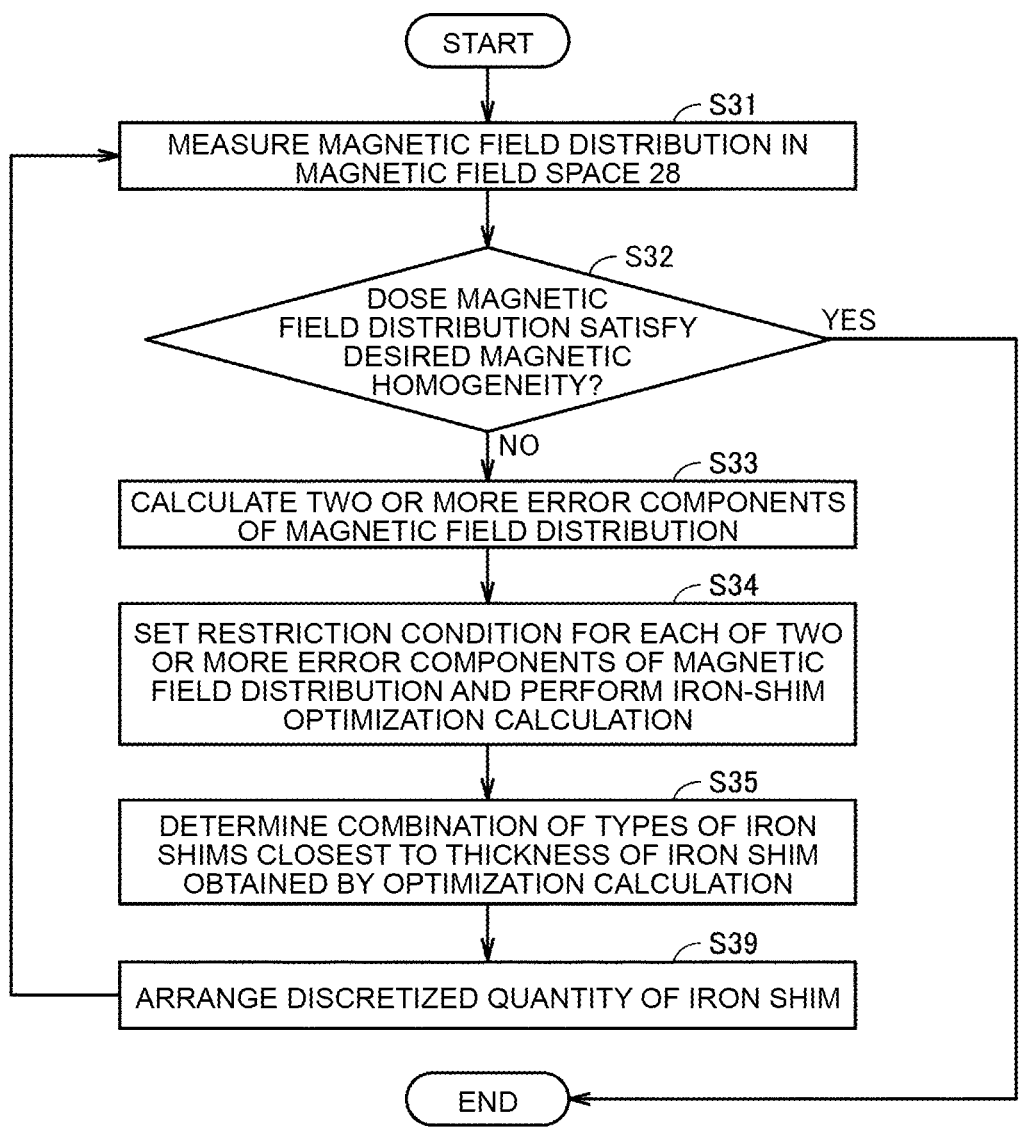
FIG. 8 is a flowchart illustrating a sequence of shimming according to a comparative example.

FIG. 8 is a flowchart illustrating a sequence of shimming according to a comparative example. The flowchart as illustrated in FIG. 8 is obtained by excluding S36 to S38 from the flowchart as illustrated in FIG. 7. S31 to S35 and S39 in FIG. 8 are the same as S31 to S35 and S39 in FIG. 7; therefore, the explanation is not repeated. The comparative example does not have any process like S38 to cancel out the discretization error of the quantity of iron shim as appropriate. Therefore, in most cases, the magnetic field distribution fails to satisfy the desired magnetic homogeneity when the iron shims are actually arranged because of the discretization error. The discretization error is cancelled out as appropriate by the shimming according to the first embodiment; thus, it becomes possible to improve the homogeneity of the magnetostatic field generated by the superconducting magnet, and it also becomes possible to reduce the number of shimming iterations required for the magnetic field distribution to reach the desired magnetic homogeneity.

The shimming according to the first embodiment can reduce the discretization error in the process of the iron-shim optimization calculation performed repeatedly. There is no need to use the thinnest iron shim, which is used for purpose of reduction of the discretization error; therefore, the variety in thicknesses of iron shims can be reduced. This, as a result, can reduce the manufacturing cost of the iron shims. This also can reduce the operation time for arranging the iron shims. Furthermore, this can reduce miscounts of the iron shims.

As described above, a method and apparatus for homogenizing a magnetostatic field generated from a superconducting magnet according to the first embodiment can improve homogeneity of the magnetostatic field formed by the superconducting magnet.

Second Embodiment

The resetting of the restriction conditions with the discretization error being taken into consideration is not limited to the plurality of error components of the magnetic field distribution. The restriction conditions may be reset on, in addition to the plurality of error components of the magnetic field distribution, the total weight of iron shims, a specific physical quantity of iron shim, such as an electromagnetic power, etc., occurred in the iron shim, or any other element. A second embodiment explains cases where a restriction condition is imposed on a physical quantity of iron shim.

Suppose, for example, the upper limit of the total weight of iron shims is 5.0 kg, and the total weight of discretized iron shims is 5.1 kg. In this example, an error of 0.1 kg beyond the upper limit of iron shims occurs due to the discretization of iron shims. The total weight of discretized iron shims can decrease to 5.0 kg or less by resetting the upper limit to 4.9 kg.

Alternatively, a similar method to the total weight of iron shims is applicable to control over an electromagnetic power occurring in the iron shims, as well. The physical quantity of iron shim can come closer to a target value by means of the setting of a restriction condition including a lower limit and an upper limit.

Figure 9:
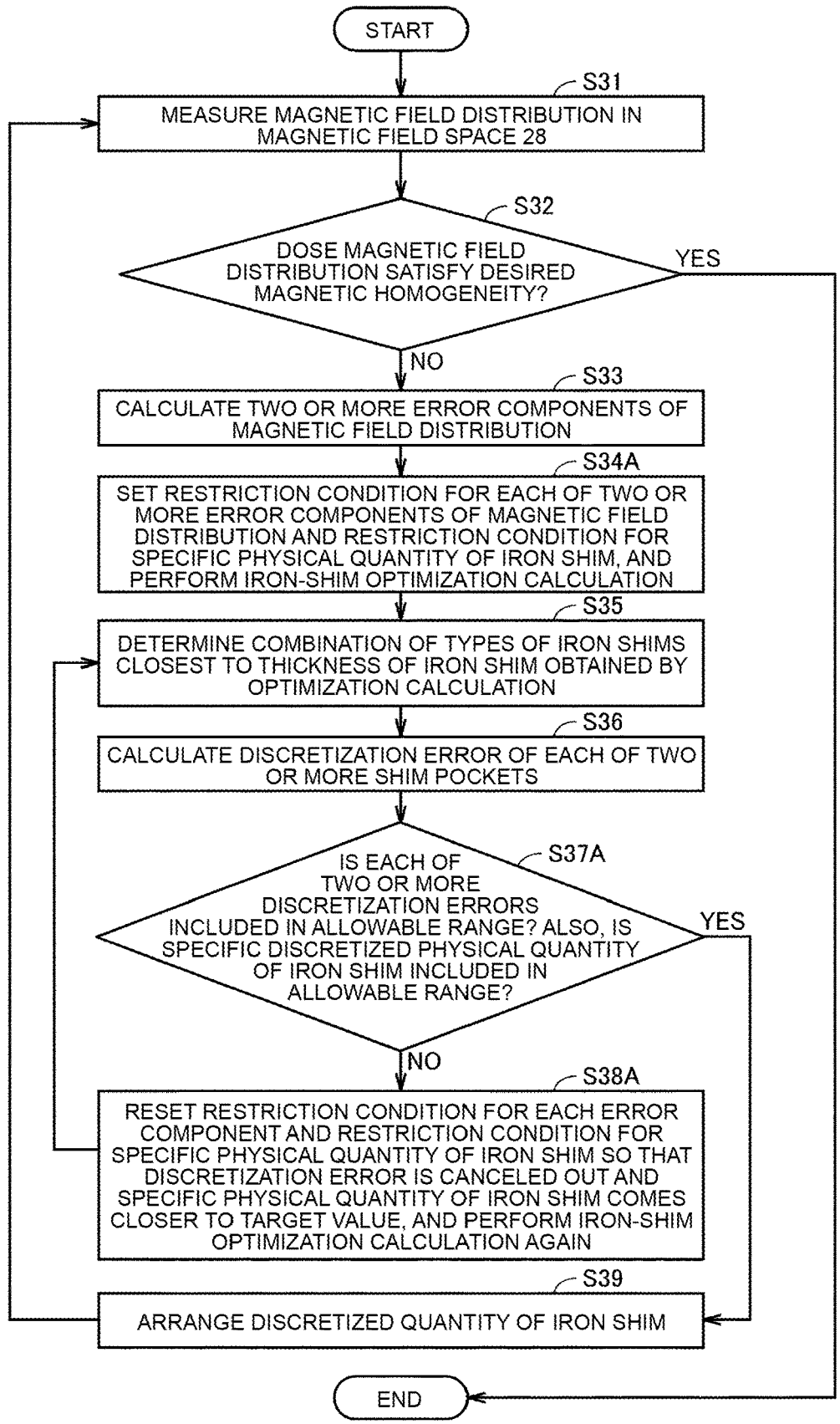
FIG. 9 is a flowchart illustrating a sequence of shimming according to a second embodiment.

FIG. 9 is a flowchart illustrating a sequence of shimming according to the second embodiment. In the flowchart as illustrated in FIGS. 9, S34, S37, and S38 of FIG. 7 are replaced with S34A, S37A, and S38A, respectively. The other steps are the same, and their explanations are not repeated.

As illustrated in FIGS. 9, S31 to S33 are performed in the same manner as described in the first embodiment; after that, at S34A, a restriction condition is set for each of the two or more error components of the magnetic field distribution, a restriction condition (third restriction condition) is set for a specific physical quantity of iron shim, and the iron-shim optimization calculation is performed.

After S35 to S36 are performed in the same manner as described in the first embodiment, it is determined at S37A whether the discretization error in the quantity of iron shim arranged in each of the plurality of shim pockets 12 is included in a predetermined allowable range and whether the specific physical discretized quantity of iron shim is included in a predetermined allowable range. When the discretization error in the quantity of iron shim arranged in each of the plurality of shim pockets 12 is included in the predetermined allowable range and the specific discretized physical discretized quantity of iron shim is included in the predetermined allowable range (YES at S37A), the quantity of iron shim discretized at S35 is actually arranged in each of the plurality of shim pockets 12 at S39, and the process returns to S31. When the discretization error in the quantity of iron shim corresponding to one of the plurality of shim pockets 12 is not included in the predetermined allowable range or when the specific physical discretized quantity of iron shim is not included in the predetermined allowable range (NO at S37A), at S38A, the restriction condition for each of the two or more error components in the magnetic field distribution and the restriction condition for the specific physical quantity of iron shim are reset so that the discretization error is cancelled out and the specific physical quantity of iron shim comes closer to the target value. At S38A, the iron-shim optimization calculation is performed again so as to satisfy the reset restriction condition for each error component and the reset restriction condition (fourth restriction condition) for iron shims. After the iron-shim optimization calculation is completed at S38A, the process returns to S35.

At S38A, the resetting of the restriction condition is performed for each of the two or more error components in the magnetic field distribution in the same manner as described in the first embodiment. In addition, at S38A, when the specific physical quantity of iron shim is greater than the upper limit (second upper limit) of the restriction condition set at S34A, a condition including an upper limit less than the upper limit of this restriction condition is reset as the restriction condition.

As described above, a method and an apparatus for homogenizing a magnetostatic field generated from a superconducting magnet according to the second embodiment can improve homogenization of the magnetostatic field generated by the superconducting magnet.

With at least one embodiment as explained above, it is possible to improve homogenization of a magnetostatic field generated by a superconducting magnet.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of homogenizing, in a specific space, a magnetostatic field generated from a superconducting magnet by arranging a plurality of ferromagnetic bodies in the specific space, the specific space being subjected to the magnetostatic field, wherein a plurality of positions in the specific space at which the plurality of ferromagnetic bodies are arranged are predetermined, and each of the plurality of ferromagnetic bodies is selected from a plurality of specific ferromagnetic bodies each having a corresponding predetermined quantity of ferromagnetic material, the method comprising:

setting a first restriction condition including a corresponding first lower limit and a corresponding first upper limit for each of a plurality of error components of a magnetic field distribution in the specific space, and calculating a respective first optimum quantity of ferromagnetic material arranged at each position of the plurality of positions so that each error component, of the plurality of error components, satisfies the first restriction condition corresponding to the error component;

calculating, for each position of the plurality of positions, a first combination of at least one ferromagnetic body selected from the plurality of specific ferromagnetic bodies, the first combination having a first total corresponding ferromagnetic material amount closest to the first respective optimum quantity corresponding to the position among all possible combinations of the at least one ferromagnetic body;

calculating the plurality of error components that result when ferromagnetic material is arranged at each of the plurality of positions in quantities specified by the calculated first combination;

when, for each error component of the plurality of error components, the calculated error component is less than the first lower limit corresponding to the error component, setting a condition including a lower limit that is greater than the first lower limit and an upper limit that is greater than the first upper limit as a second restriction condition, and when the calculated error component is greater than the first upper limit corresponding to the error component, setting a condition including a lower limit that is less than the first lower limit and an upper limit that is less than the first upper limit as the second restriction condition, and calculating a respective second optimum quantity of ferromagnetic arranged at each position of the plurality of positions so that each error component, of the plurality of error components, satisfies the second restriction condition corresponding to the error component; and calculating, for each position of the plurality of positions, a second combination of at least one ferromagnetic body selected from the plurality of specific ferromagnetic bodies, the second combination having a second total corresponding ferromagnetic material amount closest to the respective second optimum quantity corresponding to the position among all possible combinations of the at least one ferromagnetic body.

2. The method according to claim 1, wherein the calculating the respective first optimum quantity includes setting a third restriction condition including a second upper limit on a specific physical quantity of the ferromagnetic material arranged at the plurality of positions, and calculating the respective first optimum quantity so that each error component, of the plurality of error components, satisfies the first restriction condition corresponding to the error component and that the specific physical quantity satisfies the third restriction condition, and the calculating the respective second optimum quantity further comprises, when the specific physical quantity of ferromagnetic specified by the first combination is greater than the second upper limit, setting a condition including an upper limit less than the second upper limit as a fourth restriction condition, and calculating the respective second optimum quantity of the ferromagnetic material arranged at each position of the plurality of positions so that each error component of the plurality of error components satisfies the second restriction condition corresponding to the error component and that the specific physical quantity satisfies the fourth restriction condition.

3. The method according to claim 2, wherein the specific physical quantity includes a total weight of the ferromagnetic material arranged at the plurality of positions and an electromagnetic power generated at the ferromagnetic material arranged at each of the plurality of positions.

4. An apparatus for homogenizing, in a specific space, a magnetostatic field generated from a superconducting magnet by arranging a plurality of ferromagnetic bodies in the specific space, the specific space being subjected to the magnetostatic field, the apparatus comprising:

processing circuitry; and a memory configured to store a specific program therein, wherein a plurality of positions in the specific space at which the plurality of ferromagnetic bodies are arranged are predetermined, each of the plurality of ferromagnetic bodies is selected from a plurality of specific ferromagnetic bodies each having a predetermined quantity, and when executing the specific program, the processing circuitry is configured to perform:

setting a first restriction condition including a corresponding first lower limit and a corresponding first upper limit for each of a plurality of error components of a magnetic field distribution in the specific space, and calculating a respective first optimum quantity of ferromagnetic material arranged at each position of the plurality of positions so that each error component, of the plurality of error components, satisfies the first restriction condition corresponding to the error component;

calculating, for each position of the plurality of positions, a first combination of at least one ferromagnetic body selected from the plurality of specific ferromagnetic bodies, the first combination having a first total corresponding ferromagnetic material amount closest to the respective first optimum quantity corresponding to the position among all possible combinations of the at least one ferromagnetic body;

calculating the plurality of error components that result when ferromagnetic material is arranged at each of the plurality of positions in quantities specified by the calculated first combination;

when, for each error component of the plurality of error components, the calculated error component is less than the first lower limit corresponding to the error component, setting a condition including a lower limit that is greater than the first lower limit and an upper limit that is greater than the first upper limit as a second restriction condition, and when the calculated error component is greater than the first upper limit corresponding to the error component, setting a condition including a lower limit that is less than the first lower limit and an upper limit that is less than the first upper limit as the second restriction condition, and calculating a respective second optimum quantity of ferromagnetic arranged at each position of the plurality of positions so that each error component, of the plurality of error components, satisfies the second restriction condition corresponding to the error component; and calculating, for each position of the plurality of positions, a second combination of at least one ferromagnetic body selected from the plurality of specific ferromagnetic bodies, the second combination having a second total corresponding ferromagnetic material amount closest to the respective second optimum quantity corresponding to the position among all possible combinations of the at least one ferromagnetic body.

* * * * *